(12) United States Patent
Sliger (10) Patent No.: US 8,128,050 B1
(45) Date of Patent: Mar. 6, 2012

(54) ULTRASOUND SCANNER SUPPORT DEVICES

(75) Inventor: Bradley J. Sliger, Seattle, WA (US)

(73) Assignee: SonoSite, Inc., Bothell, WA (US)

( * ) Notice: Subject to any disclaimer, the term of this patent is extended or adjusted under 35 U.S.C. 154(b) by 0 days.

(21) Appl. No.: 13/023,359

(22) Filed: Feb. 8, 2011

(51) Int. Cl.
*A47B 91/00* (2006.01)

(52) U.S. Cl. ................ 248/346.03; 248/51; 248/637

(58) Field of Classification Search .......... 248/346.03, 248/346.01, 682, 688, 51, 52, 637, 676, 678
See application file for complete search history.

(56) References Cited

U.S. PATENT DOCUMENTS

| | | | | |
|---|---|---|---|---|
| 4,023,755 A | * | 5/1977 | Alesi, Jr. .................. | 248/678 |
| 4,056,251 A | * | 11/1977 | Dixon et al. ............. | 248/678 |
| 5,901,712 A | * | 5/1999 | St. Peter .................. | 132/232 |
| 7,454,852 B2 | * | 11/2008 | Giovalle et al. ......... | 38/142 |
| 2004/0069920 A1 | * | 4/2004 | Dirks ....................... | 248/316.7 |

* cited by examiner

*Primary Examiner* — Ramon Ramirez (57) ABSTRACT

Ultrasound scanner support devices and associated methods are disclosed herein. In various embodiments, an ultrasound scanner support device can include a body having a first surface and a second surface opposite the first surface. The ultrasound scanner support device can further include a recess having an interior surface between the first and second surfaces and a sidewall extending from the first surface to the interior surface. The recess can be shaped to releasably retain an ultrasound scanner connector. The ultrasound scanner support device can further include a peripheral channel extending around a perimeter of the body. The peripheral channel can have a curve at each directional change. Additionally, the ultrasound scanner support device can include a holder coupled to the body and configured to releasably retain an ultrasound scanner.

27 Claims, 6 Drawing Sheets

ULTRASOUND SCANNER SUPPORT DEVICES

TECHNICAL FIELD

The present technology is related to support devices for transporting and/or storing ultrasound scanner assemblies and associated methods of manufacturing.

BACKGROUND

Ultrasound imaging systems are widely used in medicine for visualizing tendons, muscles, joints, vessels, internal organs, and/or other subcutaneous body structures. Ultrasound imaging systems are also frequently used in obstetrics to visualize embryos or fetuses while in utero. Ultrasound imaging systems are often portable and typically include a processing station (e.g., a computer) linked to an ultrasound scanner with a cable. The cable is generally fixedly attached to the ultrasound scanner at one end and has a detachable connector configured to interface with the processing station at the other end. In operation, the connector on the cable is plugged into the processing station to provide power and allow communication between the ultrasound scanner and the processing station. The cables generally have a coaxial line for each transducer in the scanner. For example, sophisticated scanners with 128, 256 or even more transducers require cables with a corresponding number of small, relatively delicate coaxial lines.

When the ultrasound scanner is not in use (e.g., during transport and/or storage), the connector is unplugged from the processing station. According to conventional techniques, the cable is typically wrapped around the connector for transport and/or storage. However, wrapping the cable around the connector can damage the small coaxial lines in the cable. Conventional connectors, for example, have a rectangular plate-like shape with sharp edges, and bending the cable around such sharp edges can break and/or otherwise damage the small coaxial lines in the cable. This can result in failure of the ultrasound scanner and/or the ultrasound imaging system. Accordingly, there is a need for support devices that can carry ultrasound scanners for transport and/or storage without damaging the communication lines.

DETAILED DESCRIPTION

The present technology is directed to support devices that can store and transport ultrasound scanners. It will be appreciated that several of the details set forth below are provided to describe the following embodiments in a manner sufficient to enable a person skilled in the relevant art to make and use the disclosed embodiments. Several of the details described below, however, may not be necessary to practice certain embodiments of the technology. Additionally, the technology can include other embodiments that are within the scope of the claims but are not described in detail with reference to FIGS. 1A-3.

Figure 1A:
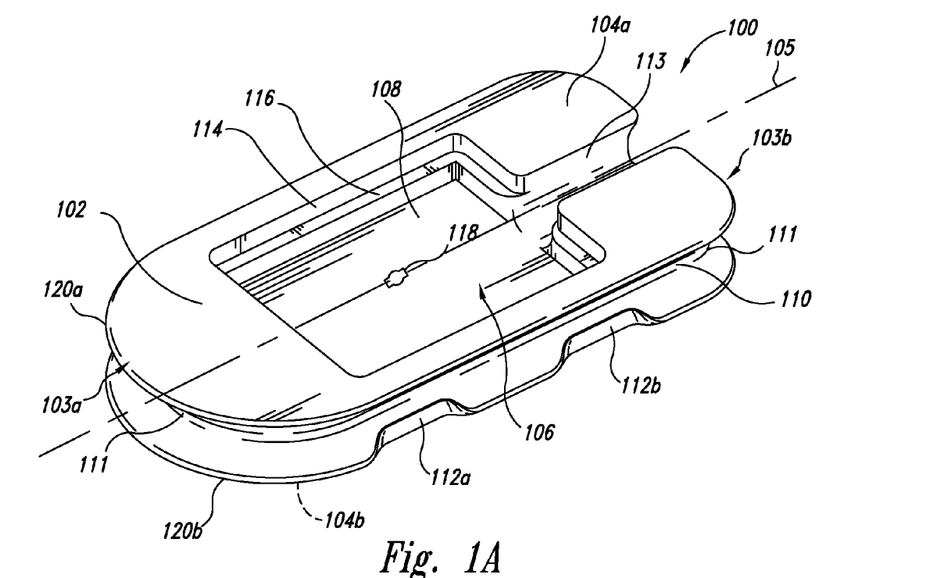
FIGS. 1A-1D are isometric, back, front, and bottom views, respectively, of a support device configured in accordance with embodiments of the present technology.

FIGS. 1A-1D are isometric, back, front, and bottom views, respectively, of a support device 100 in accordance with embodiments of the technology. As shown in FIG. 1A, the support device 100 can include a body 102, a recess 106 or other cavity in a central area of the body 102, and first and second flanges 120a-b extending away from the periphery of the body 102. In the illustrated embodiment, the body 102 and the first and second flanges 120a-b are shown as a unitary piece. In other embodiments, at least one of the first and second flanges 120a-b can be a separate component attached to the body 102 via adhesion, mechanical fastening, and/or other suitable means.

The body 102 can include a first surface 104a opposite a second surface 104b. The body 102 can also include a first end 103a and a second end 103b between the first and second surfaces 104a-b. In the illustrated embodiment, the first and second surfaces 104a-b are generally parallel to each other. In other embodiments, the first and second surfaces 104a-b may be canted relative to each other and/or may have other geometric configurations.

As shown in FIG. 1A, the recess 106 can include an interior surface 108 and a sidewall 114 that extend between the first surface 104a and the interior surface 108. In the illustrated embodiment, the recess 106 generally straddles a centerline 105 of the body 102 with the interior surface 108 substantially parallel to the first and second surfaces 104a-b. In other embodiments, the recess 106 may be offset from the centerline 105 of the body 102. In further embodiments, the interior surface 108 may be canted and/or have other geometric relations relative to the first and/or second surface 104a-b.

The recess 106 can be sized and shaped to receive an ultrasound scanner connector ("connector") of an ultrasound scanner assembly for transport and/or storage. Several examples of the connector are shown in FIGS. 2A-2E. In the illustrated embodiment shown in FIG. 1A, the recess 106 has a generally rectangular shape to receive a rectangular connector. In other embodiments, the recess 106 can have other suitable shapes configured to accommodate connectors having other shapes and/or sizes. As discussed in more detail below with reference to FIGS. 2A-2E, the support device 100 can enclose one side of the connector to protect internal circuitry of the connector when the connector is received in the recess 106.

Figure 1B:
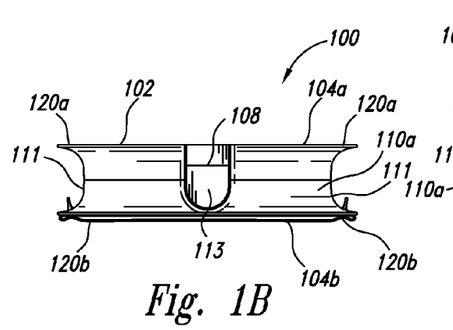
Figure 1C:
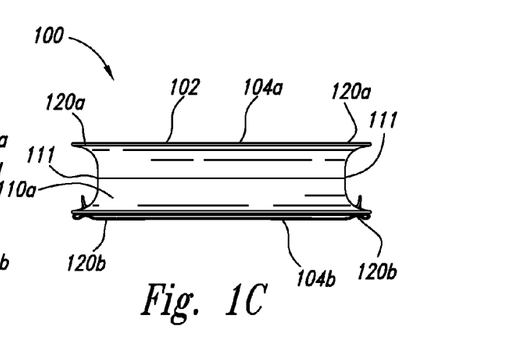

As further shown in FIGS. 1A-1C, the first and second flanges 120a-b extend beyond the body 102 and form a peripheral channel 110 therebetween. In the illustrated embodiment, the first and second flanges 120a-b are generally parallel to each other and extend beyond the body 102 by approximately the same distance. In other embodiments, at least one of the first and second flanges 120a-b may bend inward toward the peripheral channel 110 and/or may extend beyond the body 102 at a different distance than the other. In further embodiments, the first and second flanges 120a-b may have other suitable configurations.

In the illustrated embodiment, the peripheral channel 110 extends generally completely around a perimeter or circumference of the body 102 between the first and second surfaces 104a-b. In other embodiments, the peripheral channel 110 can extend around a portion of the perimeter of the body 102 and/or may have other configurations. As shown in FIGS. 1A-1D, the peripheral channel 110 does not include abrupt or acute edges at the corners. Instead, at the individual directional changes, the peripheral channel 110 has a curve 111 with a high radius of curvature to avoid over-bending or kinking a cable received therein. In some embodiments, for example, the curves 111 can have a radius of curvature of about 0.25 inch, 0.5 inch, 0.75 inch, or 1.0 inch. In other embodiments, the curves 111 can have other suitable values of radii.

As shown in FIGS. 1A and 1B, the body 102 also includes an internal channel 113 between the recess 106 and a portion of the peripheral channel 110 proximate the second end 103b of the body 102. In the illustrated embodiment, the internal channel 113 is generally aligned with the centerline 105 of the body 102 and extends generally completely between the first and second surfaces 104a-b. In other embodiments, the internal channel 113 can be offset from the centerline 105 and/or may extend partially between the first and second surfaces 104a-b. In further embodiments, the internal channel 113 can be omitted.

In the embodiment shown in FIG. 1A, the support device 100 further includes a shoulder 116 protruding inwardly from the sidewall 114 and spaced between the first surface 104a and the interior surface 108. The shoulder 116 can carry and/or mate with portions (e.g., edges, peripheral portions, bottom portions, etc.) of a scanner connector to securely attach the scanner connector within the recess 106. As shown in FIG. 1A, for example, the shoulder 116 has a rectangular shape to mate with a rectangular portion of the scanner connector. In other embodiments, the shoulder 116 can have a different shape that can carry and/or mate with portions of scanner connectors.

In further embodiments, the support device 100 can include a plurality of shoulders 116 (not shown) positioned at different elevations within the recess 106. The individual shoulders 116 can mate with a particularly shaped scanner connector and/or accommodate a particularly sized scanner connector. For example, each shoulder 116 can carry a scanner connector having a differently sized surface area such that the shoulder 116 nearest the first surface 104a can carry the scanner connector having a larger surface area, and the shoulder 116 nearest the interior surface 108 can carry the scanner connector having a smaller surface area. In yet further embodiments, the shoulder 116 may be omitted.

As shown in FIG. 1A, the support device 100 can also include an optional aperture 118 extending from the interior surface 108 to the second surface 104b. As described in greater detail below with reference to FIG. 2C, the aperture 118 can be shaped to receive at least a portion of a locking mechanism on the scanner connector to releasably secure the scanner connector to the support device 100. In other embodiments, aperture 118 may be omitted, and the scanner connector can be secured to the recess 106 using snaps, elastic bands, and/or other fasteners.

Figure 1D:
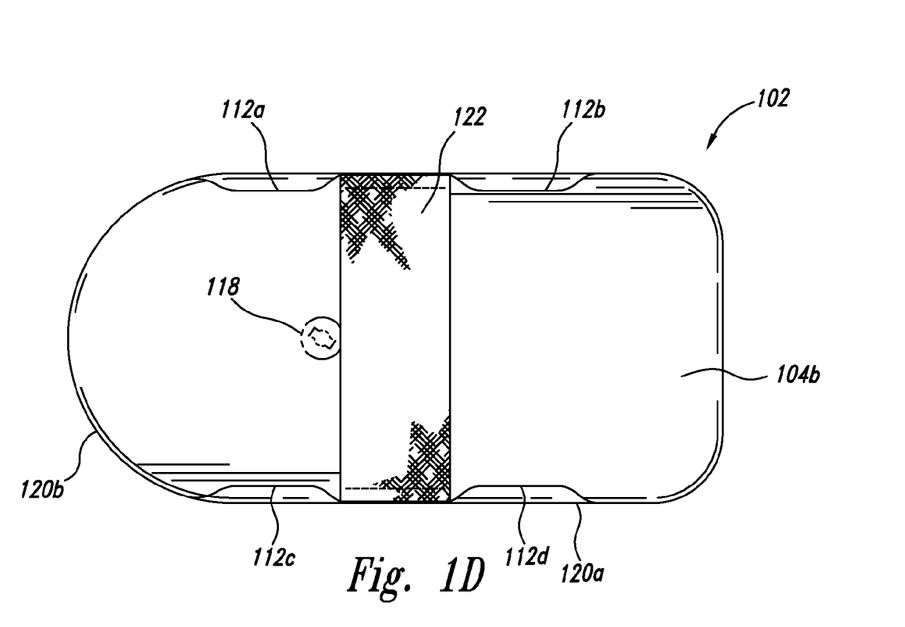

As shown in FIG. 1D, the support device 100 can include at least one notch 112 (e.g., the first and second notches 112a-b on one side, and third and fourth notches 112c and 112d on the other side) discretely spaced on the second flange 120b. The individual notches 112 can include a substantially smooth curved surface such that a cable may smoothly pass from the peripheral channel 110 to the second surface 104b via one of the notches 112. In other embodiments, at least one of the notches 112 may be positioned on the first flange 120a. As explained in greater detail with reference to FIGS. 2D and 2E, the discrete placement of the notches 112 may accommodate different lengths of cables. However, in further embodiments, the notches 112 may be omitted.

As further shown in FIG. 1D, the support device 100 can also include a holder 122 coupled to the second surface 104b of the body 102. The holder 122 can be fastened to the body 102 using stitches, adhesives, screws, and/or other suitable fasteners. In the embodiment illustrated in FIG. 1D, the holder 122 is an elastic band through which ultrasound scanners ("scanners") can be inserted and secured. In other embodiments, the holder 122 can be a pouch and/or other fasteners or storage devices that can secure a scanner to the support device 100. In further embodiments, the holder 122 can include a rigid support fixed to the body 102, as discussed in more detail later with reference to FIG. 3.

The support device 100 can be made from a lightweight, durable material that can retain an ultrasound scanner assembly during transport and/or storage. Suitable materials include, for example, plastic, wood, and/or other suitable lightweight and durable materials. In some embodiments, the sidewall 114 and/or shoulder 116 can include a deformable material (e.g., foam) that can conform to the shape of the connector and secure it within the recess 106. Additionally, the interior surface 108 can include a soft material (e.g., felt) to cushion connectors. The body 102, sidewall 114, shoulder 116, flanges 120, and/or the peripheral and internal channels 110 and 113 can be formed integrally using a molding process. In other embodiments, the features of the support device 100 can be separate components that are adhered or otherwise and fastened together.

Figure 2A:
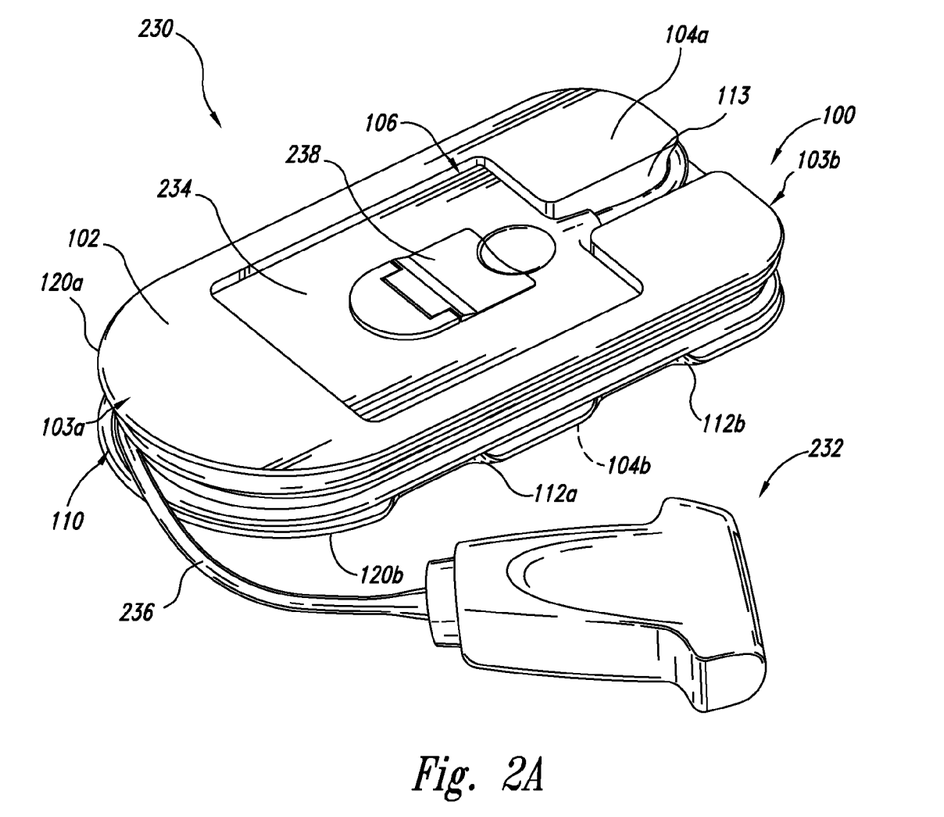
FIG. 2A is an isometric view of an ultrasound scanner assembly and the support device of FIGS. 1A-1D in accordance with embodiments of the present technology.

The support device 100 allows users to safely store and/or transport ultrasound scanner assemblies when they are not in use. For example, FIGS. 2A-2D show an ultrasound scanner assembly 230 ("scanner assembly 230") placed in the support device 100 of FIGS. 1A-1D in accordance with embodiments of the technology. Referring to FIG. 2A the scanner assembly 230 includes an ultrasound scanner 232 ("scanner 232"), a connector 234, and a cable 236 having a plurality of small wires (e.g., not shown) that independently connect individual transducer elements in the scanner 232 to processing circuitry housed in the connector 234. As shown in FIG. 2A, the connector 234 can also include a locking mechanism 238 that releasably secures the connector 234 to a corresponding portion of a processing station during an ultrasound scan.

Figure 2B:
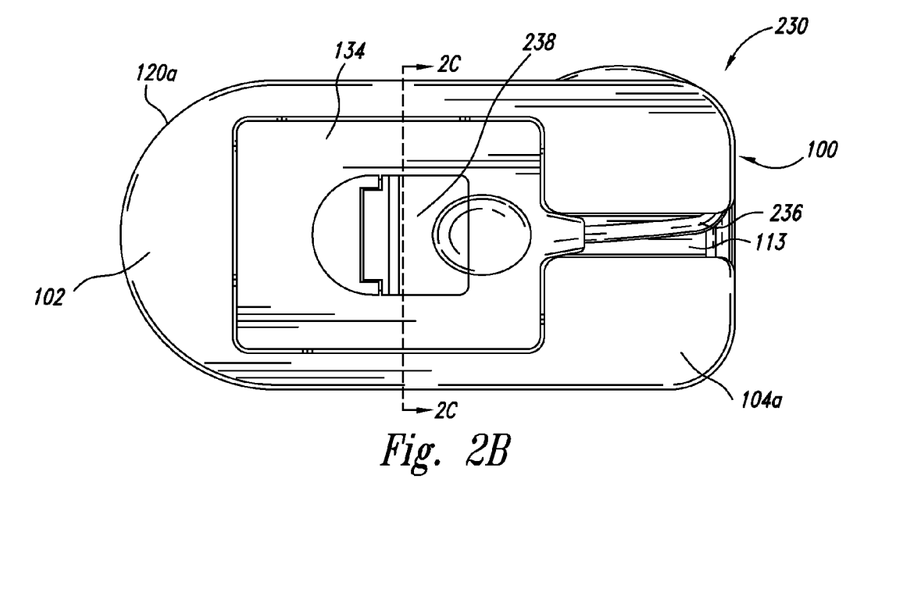
FIG. 2B is a top view of the ultrasound scanner assembly and the support device of FIG. 2A in accordance with embodiments of the present technology.

When the connector 234 is disengaged from the processing station, the connector 234 can be secured at least partially within the recess 106 as shown in FIGS. 2A and 2B. The cable 236 can extend from the connector 234, through the internal channel 113, into the peripheral channel 110, and around the perimeter of the body 102. The curves 111 of the peripheral channel 110 can at least substantially prevent communication wires housed within the cable 236 from sharply bending, kinking, cracking, or breaking.

In the illustrated embodiment shown in FIGS. 2A and 2B, the connector 234 is stored completely within the recess 106 such that the top of the connector 234 is below the first surface 104a of the body 102. In other embodiments, the connector 234 can be larger or smaller such that the connector 234 protrudes above the first surface 104a, sits flush with the first surface 104a, and/or fills less area within the recess 106.

Figure 2C:
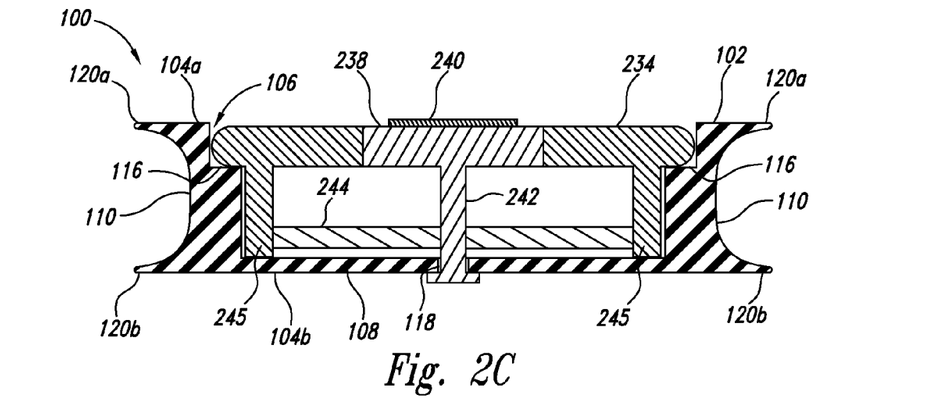
FIG. 2C is a cross-sectional view taken substantially along the line 2C-2C of FIG. 2B.

FIG. 2C is a cross-sectional view of the connector 234 securely retained in the recess 106 of the support device 100 taken substantially along the line 2C-2C of FIG. 2B. In one embodiment, the locking mechanism 238 that connects the connector 234 to the processing station also secures the connector 234 within the recess 106 of the support device 100. The locking mechanism 238 can include a handle portion 240 at the upper surface of the connector 234 and a pin portion 242 that traverses through the connector 234. As shown in FIG. 2C, the pin portion 242 can extend through the aperture 118 at the interior surface 108 of the body 102 and interlock or engage the second surface 104b of the body 102. In other embodiments, the pin portion 242 can engage another portion of the support device 100. For example, the interior surface 108 can include a recessed area configured to engage with the pin 242 such that the pin 242 extends only partially through the body 102 and does not penetrate the second surface 104b. In operation, a user can turn handle portion 240 to rotate the pin portion 242 and latch the connector 234 within the recess 106 of the support device 100.

As shown in FIG. 2C, the shoulder 116 can contact a corresponding flange 239 around the connector 234 when the locking mechanism 238 is engaged with the support device 100. The flange 239 can be configured to at least substantially mate with the upper part of the recess 196 such that the support device 100 retains the connector 234 within the safety of the recess 106.

As further shown in FIG. 2C, the substantially solid interior surface 108 can enclose circuitry 244 at the underside of the connector 234 when the connector 234 is secured in the recess 106. In some embodiments, the connector 234 has sidewalls 245 that seal against the interior surface 108 when the locking mechanism 238 is engaged. Thus, the interior surface 108 can prevent the circuitry 244 from exposure to dust, other particles, and/or moisture that may interfere with the operability of the circuitry 244. The interior surface 108 can also protect the circuitry 244 from puncture and/or other forces that may perforate the circuitry 244 and affect its functionality. Moreover, the support device 100 as a whole can provide a protective barrier around the connector 234 during handling such that the support device 100, not the connector 234, absorbs impacts.

Figure 2D:
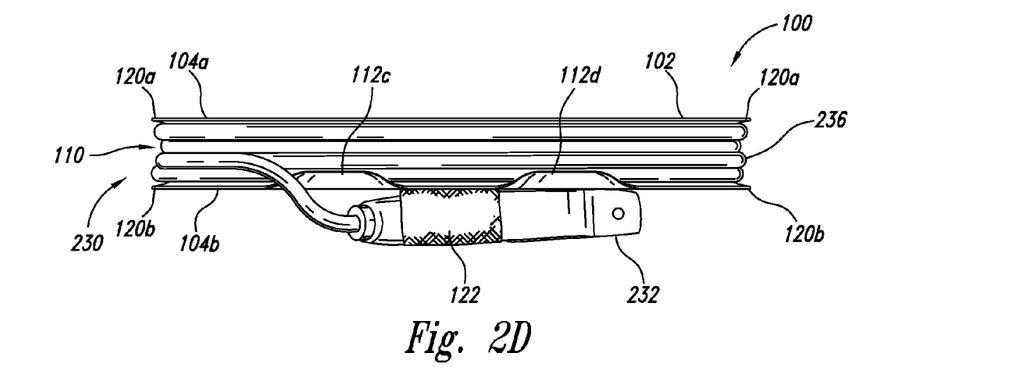
FIGS. 2D and 2E are side and bottom views, respectively, of the ultrasound scanner assembly and the support device shown in FIG. 2A.
Figure 2E:
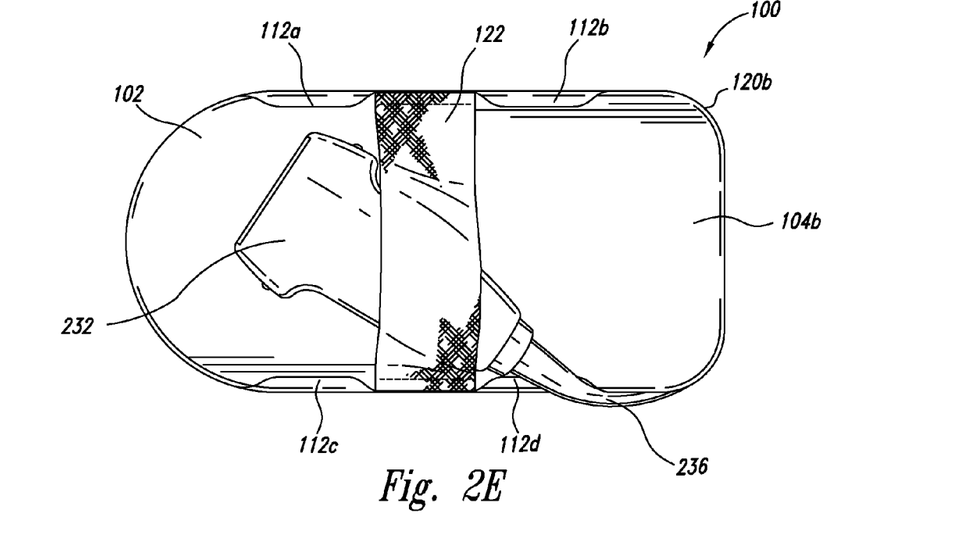

FIGS. 2D and 2E are side and bottom views of the scanner 232 and the cable 236 secured to the support device 100. Referring the FIG. 2D, the cable 236 can wrap around the peripheral channel 110 and smoothly pass over the curves 111 (not visible) at each corner of the peripheral channel 110, and the flanges 120 can confine the cable 236 within the peripheral channel 110. In the illustrated embodiment, the cable 236 passes through the curved surface of the fourth notch 112d to the second surface 104b of the body 102. If the cable 236 was shorter, longer, and/or wound more or less tightly, the cable 236 could extend through a different notch 112 to smoothly transition from the peripheral channel 110 to the second surface 104b.

As shown in FIGS. 2D and 2E, the scanner 232 can be positioned through the holder 122 at the second surface 104b of the body 102 to compactly secure the scanner 232 to the support device 100. The elasticity of the holder 122 allows the support device 100 to accommodate differently sized scanners 232.

In operation, the support device 100 can transport scanner assemblies 230 having different sizes such as for use with portable ultrasound scanning devices. For example, the shoulder 116 and the notches 112 allow the support device 100 to accommodate differently sized scanner connectors and cables, respectively. Additionally, the support device 100 can be integrated into shipping methods to encourage end users to store and transport scanner assemblies in the support device 100. The support device 100 can also be compact, lightweight, and durable to further ease transport and storage. For example, in some embodiments, the support device 100 can be made from plastic and can be 9.5 inches long, 4.5 inches wide, and 1 inch thick.

Figure 3:
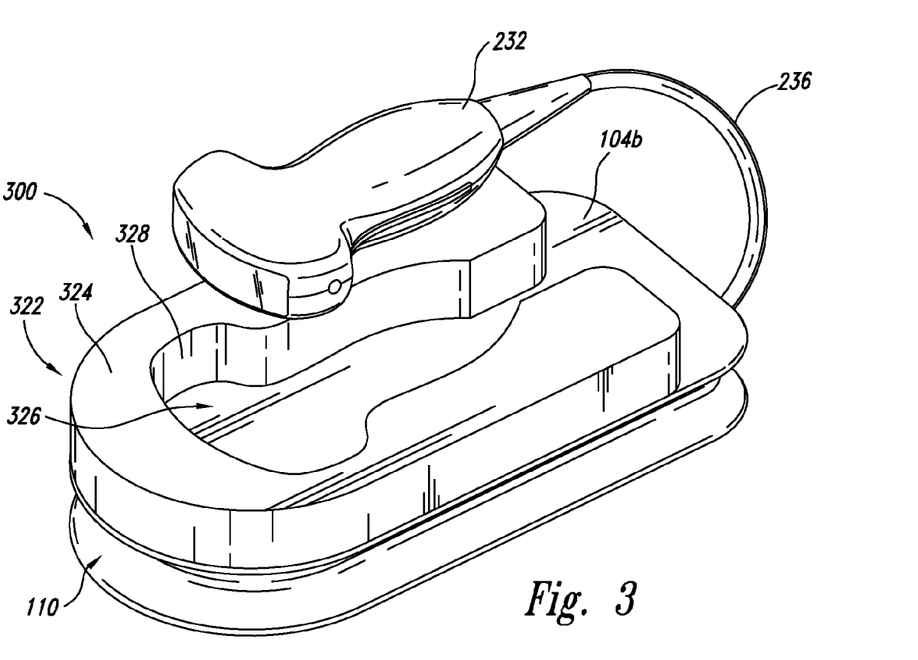
FIG. 3 is an isometric view of an ultrasound scanner and a support device configured in accordance with additional embodiments of the present technology.

FIG. 3 is an isometric view of a support device 300 configured in accordance with other embodiments of the technology. The support device 300 can include generally similar features as the support device 100 described in FIGS. 1A-2E. For example, the support device 300 can include the body 102 having the first and second surfaces 104a-b, the recess 106 (not visible) at the first surface 104a, and the peripheral channel 110 extending around the perimeter of the body 102.

The support device 300 further includes a holder 322 fixed to or otherwise extending from the second surface 104b of the body 102 that can releasably retain the scanner 232. The holder 322 can be a substantially rigid support that includes a top surface 324 and a recess 326 extending from the top surface 324 to the second surface 104b of the body 102. In other embodiments, the recess 326 can extend to an intermediate depth between the top surface 324 and the second surface 104b or beyond the second surface 104b to at most the interior surface 108. As shown in FIG. 3, the recess 326 can include a sidewall 328 shaped generally similar to the scanner 232 such that the scanner 232 can at least substantially mate with the holder 322.

In some embodiments, the holder 322 includes shoulders (not shown) generally similar to the shoulders 116 described above with reference to FIGS. 1A and 2C. The shoulders can protrude from the sidewall 328 and can be shaped to carry and/or mate with differently shaped scanners. Additionally, the shoulders can be configured to receive consecutively smaller scanners 232 deeper within the recess 354. For example, a shoulder near the second surface 104b of the body 102 can be shaped to carry and/or mate with a small scanner used for internal scanning (e.g., prostate transducers, obstetrics/gynecology transducers) and a second shoulder closer to the top surface 324 can be shaped to carry and/or mate with the larger T-shaped scanner 232 shown in FIG. 3.

In other embodiments, the holder 322 can further include a fastener to secure the scanner 232 to the support device 300. For example, the holder 322 can include an elastic material extending over the recess 326, a strap at the second surface 104b that can encircle a portion of the scanner 232, and/or other fasteners that can releasably secure the scanner 232 at least substantially within the holder 322.

The holder 322 can be fixed to the second surface 104b of the body 102 using an adhesive, a mechanical interface, and/or another suitable fastener that can join the holder 322 to the body 102. In other embodiments, the body 102 and the holder 322 can be formed integrally. Similar to the body 102, the holder 322 can be made from a generally rigid, lightweight, and durable material. For example, in some embodiments, the holder 322 is made from plastic. In other embodiments, the holder 322 and/or portions of the holder 322 (e.g., the sidewall 328) can be made from a deformable material, such as foam, that can conform to and releasably receive the scanner 232.

From the foregoing, it will be appreciated that specific embodiments of the technology have been described herein for purposes of illustration, but that various modifications may be made without deviating from the technology. For example, the embodiments illustrated above include a holder at the second surface of the body. However, other embodiments of the technology can include a holder connected to anther surface (e.g., the first surface) of a support device. Certain aspects of the technology described in the context of particular embodiments may be combined or eliminated in other embodiments. For example, the holder 322 illustrated in FIG. 3 can extend to the second end 103b of the second surface 104b of the body 102. Additionally, rather than the plurality of discrete notches 112 on each side of the support device 100 shown in FIGS. 1A-2E, a single notch can extend along almost the complete length of a side of the support device 100 to accommodate different cable lengths. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. An ultrasound scanner support device, comprising:
   a body having a first surface and a second surface opposite the first surface;
   a recess having an interior surface between the first and second surfaces and a sidewall extending from the first surface to the interior surface; and
   a peripheral channel extending around a perimeter of the body and having a curve at each directional change, wherein each curve has a radius of at least approximately 0.25 inch.

2. The ultrasound scanner support device of claim 1 wherein the ultrasound scanner support device further comprises:
   a first flange extending beyond the perimeter of the body, the first flange being proximate to the first surface;
   a second flange extending beyond the perimeter of the body, the second flange being proximate to the second surface, wherein the peripheral channel is between the first and second flanges;
   a shoulder protruding from the sidewall and partially into the opening;
   a holder connected to the second surface of the body;
   a plurality of discrete notches between the peripheral channel and the second surface, wherein each notch includes a curved surface; and
   an internal channel extending between the recess and a portion of the peripheral channel.

3. The ultrasound scanner support device of claim 1, further comprising:
   a holder coupled to the body, the holder being configured to releasably retain an ultrasound scanner.

4. The ultrasound scanner support device of claim 3 wherein the holder is an expandable band connected to the second surface of the body.

5. The ultrasound scanner support device of claim 1, further comprising:
   a shoulder protruding from the sidewall partially into the opening.

6. The ultrasound scanner support device of claim 5 wherein the shoulder is one of a plurality of shoulders spaced at different elevations within the opening, and the plurality of shoulders protrude further into the recess as the shoulders are spaced closer to the interior surface.

7. The ultrasound scanner support device of claim 1, further comprising:
   a notch spaced between the peripheral channel and at least one of the first and second surfaces, the notch having a curved surface.

8. The ultrasound scanner support device of claim 7 wherein the notch is one of a plurality of discrete notches, and wherein the ultrasound scanner support device further comprises:
   a flange projecting beyond the perimeter of the body proximate to the second surface of the body, wherein the plurality of notches are on the second flange.

9. The ultrasound scanner support device of claim 1, further comprising:
   a flange extending beyond the perimeter of the body, the flange being configured to retain a cable within the peripheral channel.

10. The ultrasound scanner support device of claim 1 wherein the interior surface is substantially solid and at least substantially parallel to the first surface of the body.

11. The ultrasound scanner support device of claim 1, further comprising:
    an aperture extending from the interior surface to the second surface.

12. The ultrasound scanner support device of claim 1, further comprising:
    an internal channel extending from the recess to a portion of the peripheral channel.

13. The ultrasound scanner support device of claim 1, further comprising:
    a holder at the second surface of the body, the holder having a top surface spaced longitudinally apart from the second surface and a recess extending between the top surface and the second surface of the body, wherein the recess has a generally similar shape as a periphery of an ultrasound scanner.

14. An ultrasound scanner support device, comprising:
    a body having a first surface, a second surface opposite the first surface, and a recess at the first surface, wherein the recess includes a sidewall extending from the first surface to an interior surface between the first and second surfaces, and wherein the recess is configured to receive an ultrasound scanner connector;
    a peripheral channel extending around a perimeter of the body, the peripheral channel having a curve at each corner and being configured to receive a cable connecting the ultrasound scanner connector to an ultrasound scanner; and
    a notch between the peripheral channel and the second surface of the body, the notch having a curved surface and being configured to transition the cable from the peripheral channel to the second surface.

15. The ultrasound scanner support device of claim 14, further comprising:
    a shoulder protruding from the sidewall into the opening, the shoulder being shaped to carry a portion of the ultrasound scanner connector.

16. The ultrasound scanner support device of claim 14, further comprising:
    a holder having a top surface spaced longitudinally apart from the second surface of the body and a recess extending from the top surface to at most the interior surface, the recess being shaped receive the ultrasound scanner.

17. The ultrasound scanner support device of claim 14, further comprising:
    a first flange extending from the first surface beyond the perimeter of the body;
    a second flange extending from the second surface beyond the perimeter of the body, wherein the peripheral channel is between the first and second flanges.

18. The ultrasound scanner support device of claim 14, further comprising:
    an internal channel extending from the recess to a portion of the peripheral channel.

19. A method of manufacturing an ultrasound scanner support device, the method comprising:
    forming a body, the body having a first surface and a second surface opposite the first surface;

forming a recess at the first surface of a body, wherein the recess extends from the first surface to an interior surface between the first and second surfaces; and forming a peripheral channel extending around a perimeter of the body, the peripheral channel having a curve at each corner.

20. The method of claim 19 wherein forming the recess further comprises:

forming a sidewall extending from the first surface to the interior surface; and forming a shoulder protruding from the sidewall into the opening, the shoulder being shaped to carry a portion of a scanner connector.

21. The method of claim 19, further comprising:

forming an aperture extending from the interior surface to the second surface, the aperture being configured to secure the ultrasound scanner connector to the ultrasound support device.

22. The method of claim 19, further comprising:

connecting a holder to at least one of the first and second surfaces of the body, wherein the holder includes an elastic band configured to releasably retain an ultrasound scanner.

23. The method of claim 19, further comprising:

connecting a holder to the second surface of the body, the holder being substantially rigid and including a top surface spaced longitudinally apart from the second surface; and forming a recess extending from the top surface of the support to at most the interior surface of the body, the recess having a sidewall shaped generally similar as a shape of an ultrasound scanner.

24. The method of claim 19, further comprising:

forming an internal channel extending from the recess to the peripheral channel.

25. The method of claim 19, further comprising:

forming a plurality of notches between the peripheral channel and at least one of the first and second surfaces of the body, wherein the notches have curved surfaces.

26. The method of claim 19 wherein forming the peripheral channel includes forming the curves to have a radius of at least approximately 0.25 inch.

27. The method of claim 19 wherein forming the peripheral channel comprises:

forming a first flange extending beyond a perimeter of the body, the first flange being proximate to the first surface of the body; and forming a second flange extending beyond the perimeter of the body, the second flange being proximate to the second surface of the body, wherein the peripheral channel is between the first and second flanges.

\* \* \* \* \*